United States Patent
Holton et al.

(10) Patent No.: US 6,291,692 B1
(45) Date of Patent: Sep. 18, 2001

(54) 9-DESOXOBACCATIN III AND ANALOGS THEREOF

(75) Inventors: Robert A. Holton; Carmen Somoza; Yukio Suzuki; Mitsuru Shindo, all of Tallahassee, FL (US)

(73) Assignee: Florida State University, Tallahassee, FL (US)

( * ) Notice: Subject to any disclaimer, the term of this patent is extended or adjusted under 35 U.S.C. 154(b) by 0 days.

(21) Appl. No.: 09/689,400

(22) Filed: Oct. 12, 2000

Related U.S. Application Data

(60) Continuation of application No. 09/356,097, filed on Jul. 16, 1999, now Pat. No. 6,147,234, which is a division of application No. 08/026,978, filed on Mar. 5, 1993, now Pat. No. 5,990,325.

(51) Int. Cl.$^7$ .................................................. C07D 305/14
(52) U.S. Cl. ........................................... 549/510; 549/511
(58) Field of Search ..................................... 549/510, 511

(56) References Cited

U.S. PATENT DOCUMENTS

| | | |
|---|---|---|
| 4,814,470 | 3/1989 | Colin et al. . |
| 4,876,399 | 10/1989 | Holton et al. . |
| 4,921,974 | 5/1990 | Duggan . |
| 4,924,011 | 5/1990 | Denis et al. . |
| 4,924,012 | 5/1990 | Colin et al. . |
| 5,175,315 | 12/1992 | Holton . |
| 5,352,806 | 10/1994 | Gunawardana et al. . |
| 5,440,056 | 8/1995 | Klein et al. . |
| 5,468,769 | 11/1995 | Klein et al. . |
| 5,530,020 | 6/1996 | Gunawardana et al. . |
| 5,594,157 | 1/1997 | Gunawardana et al. . |
| 5,616,740 | 4/1997 | Klein et al. . |

FOREIGN PATENT DOCUMENTS

WO 99/37631    7/1999   (WO) .

OTHER PUBLICATIONS

Chen et al. "Taxol Structure–Activity Relationships: Synthesis and Biological Evaluation of 2–Deoxytaxol" Tetrahedron Letters, vol. 34, No. 20 (1993) pp. 3205–3206.

Denis et al. A Highly Efficient, Practical Approach to Natural Taxol, Journal of American Chemical Society, vol. 110, No. 17 (1988) pp. 5917–5919.

Farina et al. "The Chemistry of Taxanes: Unexpected Rearrangement of Baccatin III During Chemoselective Debenzoylation with Bu3SnOMe/LiCl" Tetrahedron Letters, vol. 33, No. 28 (1992) pp. 3979–3982.

Holton et al. "A Synthesis of Taxusin" Journal of American Chemical Society, vol. 110 (1988) pp. 6558–6560.

Kingston et al. "The Taxane Diterpenoids" Progress in the Chemistry of Organic Natural Products 61, (1993) pp. 73–75, Springer–Verlag, New York.

Klein et al. "Synthesis of 9–Dihydrotaxol: A Novel Bioactive Taxane" Tetrahedron Letters, vol. 34, No. 13 (1993) pp. 2047–2050.

Miller et al. "Antileukemic Alkaloids from Taxus Wallichiana Zucc" Journal of Organic Chemistry, vol. 45, No. 7 (1981) pp. 1469–1474.

Samaranayake et al. "Modified Taxols. 5.1 Reaction of Taxol with Electrophillic Reagents and Preparation of a Rearranged Taxol Derivative with Tubulin Assembly Activity 3" Journal of Organic Chemistry, vol. 56, No. 17 (1991) pp. 5114–5119.

*Primary Examiner*—Ba K. Trinh
(74) *Attorney, Agent, or Firm*—Senniger, Powers, Leavitt & Roedel

(57) ABSTRACT

Process for the preparation of a derivative or analog of baccatin III or 10-desacetyl baccatin III having a C9 substituent other than keto in which the C9 keto substituent of taxol, a taxol analog, baccatin III or 10-desacetyl baccatin III is selectively reduced to the corresponding hydroxy group.

19 Claims, No Drawings

9-DESOXOBACCATIN III AND ANALOGS THEREOF

REFERENCE TO RELATED APPLICATIONS

This application is a continuation of U.S. patent application Ser. No. 09/356,097, filed Jul. 16, 1999, now U.S. Pat. No. 6,147,234, which is a divisional of U.S. Ser. No. 08/026,978, filed Mar. 5, 1993, now U.S. Pat. No. 5,990,325.

BACKGROUND OF THE INVENTION

The present invention relates to a process for the preparation of taxol, baccatin III and 10-desacetylbaccatin III derivatives or analogs having new C9 functional groups.

Taxol is a natural product extracted from the bark of yew trees. It has been shown to have excellent antitumor activity in in vivo animal models, and recent studies have elucidated its unique mode of action, which involves abnormal polymerization of tubulin and disruption of mitosis. It is currently undergoing clinical trials against ovarian, breast and other types of cancer in the United States and France and preliminary results have confirmed it as a most promising chemotherapeutic agent. The structure of taxol and the numbering system conventionally used is shown below; this numbering system is also applicable to compounds used in the process of the present invention.

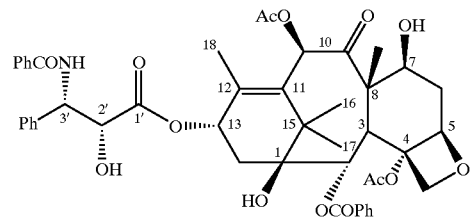

In Colin U.S. Pat. No. 4,814,470, it was reported that a taxol derivative, commonly referred to as taxotere, has an activity significantly greater than taxol. Taxotere has the following structure:

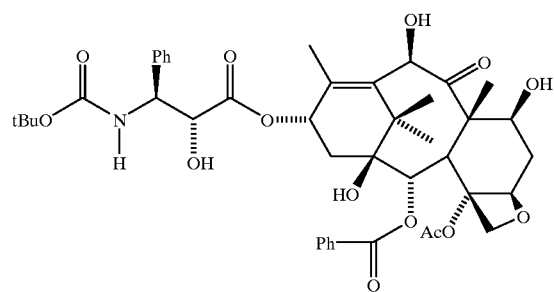

In copending application, U.S. Ser. No. 07/949,449, filed Sep. 22, 1992, it is reported that 10-desacetoxytaxol and related compounds also exhibit anti-tumor activity. Compounds disclosed in this copending application include:

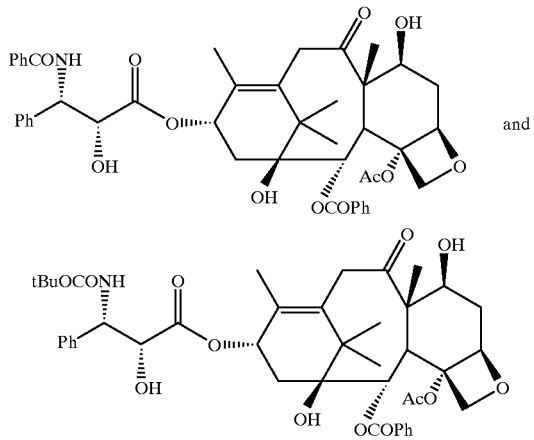

Taxol, taxotere and other biologically active tetracyclic taxanes may be prepared semisynthetically from baccatin III and 10-desacetyl baccatin III as set forth in U.S. Pat. Nos. 4,924,011 and 4,924,012 or by the reaction of a β-lactam and a suitably protected baccatin III or 10-desacetylbaccatin III ("10-DAB") derivative as set forth in U.S. Pat. No. 5,175,315 or copending U.S. patent application Ser. No. 07/949,107 (which is incorporated herein by reference). Baccatin III 1 and 10-DAB 2 can be separated from mixtures extracted from natural sources such as the needles, stems, bark or heartwood of numerous Taxus species and have the following structures.

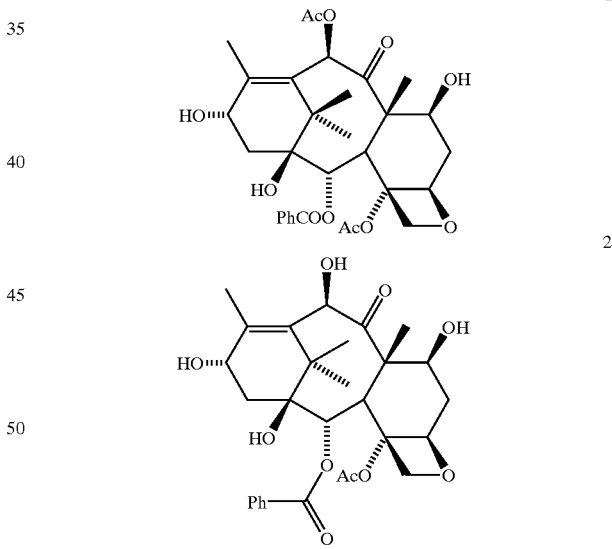

The tetracyclic core of taxol and taxotere bear a C9 keto substituent which, if modified, would lead to the preparation of a series of taxol analogs having improved water solubility. To date, however, the selective manipulation of the C9 keto group has presented a formidable problem.

SUMMARY OF THE INVENTION

Among the objects of the present invention, therefore, is the provision of a process for selectively manipulating the C9 keto substituent of baccatin III and analogs or derivatives thereof; and the provision of such a process which is relatively straightforward.

Briefly, therefore, the present invention is directed to a process for the preparation of analogs or derivatives of taxol, baccatin III or 10-desacetyl baccatin III in which the C9 keto substituent is reduced to the corresponding hydroxy group. Optionally, the C9 hydroxy substituent may thereafter be selectively replaced by another functional group and/or other substituents of the tetracyclic taxane may be replaced by other functional groups to yield a tetracyclic taxane having the formula

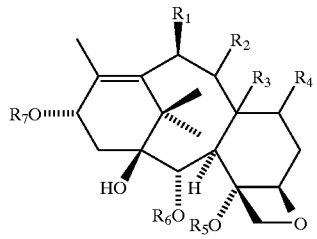

wherein $R_1$ is H, —OH, protected hydroxy, or —OCOR$_8$,
$R_2$ is H, —OH, or acyloxy,
$R_3$ is methyl,
$R_4$ is H, —OH or protected hydroxy;
$R_5$ is H or $R_9$CO—,
$R_6$ is H or $R_{10}$(CO—,
$R_7$ is H, a hydroxy protecting group, or

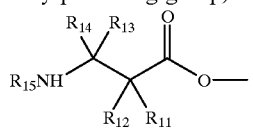

$R_8$ $R_9$, and $R_{10}$, are independently H, $C_1$–$C_6$ alkyl, $C_2$–$C_6$ alkenyl, $C_2$–$C_6$ alkynyl, moncyclic aryl, or monocyclic heteroaryl.
$R_{11}$ is —OR$_{16}$, —SR$_{17}$, or —NR$_{18}$R$_{19}$;
$R_{12}$ is hydrogen, alkyl, alkenyl, alkynyl, aryl or heteroaryl;
$R_{13}$ and $R_{14}$ are independently hydrogen, alkyl, or alkenyl, alkynyl, aryl, acyl or heteroaryl, provided $R_{13}$ and $R_{14}$ are not both acyl;
$R_{15}$ is —COR$_{20}$, —CCOR$_{20}$, —COSR$_{20}$, —CONR$_{14}$R$_{20}$, or —SO$_2$R$_{21}$
$R_{16}$ is hydrogen, alkyl, alkenyl, alkynyl, aryl, heteroaryl, or hydroxy protecting group,
$R_{17}$ is alkyl, alkenyl, alkynyl, aryl, heteroaryl, or sulfhydryl protecting group,
$R_{18}$ is hydrogen, alkyl, alkenyl, alkynyl, aryl, or heteroaryl;
$R_{19}$ is an amino protecting group;
$R_{20}$ is alkyl, alkenyl, alkynyl, aryl, or heteroaryl, and
$R_{21}$ is alkyl, alkenyl, alkynyl, aryl, heteroaryl, —OR$_{17}$, or —NR$_{14}$R$_{18}$.

The present invention is additionally directed to a derivative of baccatin III or 10-desacetyl baccatin III having the following formula which is a key intermediate in the synthesis of a new series of tetracyclic taxanes

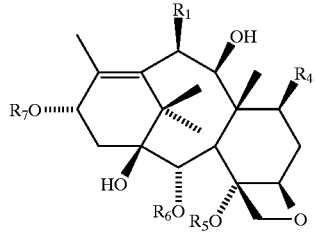

wherein $R_1$, $R_4$, $R_5$ and $R_6$ are as previously defined and $R_7$ is hydrogen or a hydroxy protecting group.

Other objects and features of this invention will be in part apparent and in part pointed out hereinafter.

DETAILED DESCRIPTION OF THE INVENTION

As used herein "Ar" means aryl; "Ph" means phenyl; "Ac" means acetyl; "Et" means ethyl; "R" means alkyl unless otherwise defined; "tBu" means t-butyl; "TES" means triethylsilyl; "TMS" means trimethylsilyl; "TPAP" means tetrapropylammonium perruthenate; "DMAP" means p-dimethylamino pyridine; "DMF" means dimethylformamide; "LDA" means lithium diisopropylamide; "LAH" means lithium aluminum hydride; "Red-Al" means sodium bis(2-methoxyethoxy) aluminum hydride; "10-DAB" means 10-desacetylbaccatin III; protected hydroxy means —OR wherein R is a hydroxy protecting group; sulfhydryl protecting group" includes, but is not limited to, hemithioacetals such as 1-ethoxyethyl and methoxymethyl, thioesters, or thiocarbontates; "amine protecting group" includes, but is not limited to, carbamates, for example, 2,2,2-trichloroethylcarbamate or tertbutylcarbamate; and "hydroxy protecting group" includes, but is not limited to, ethers such as methyl, t-butyl, benzyl, p-methoxybenzyl, p-nitrobenzyl, allyl, trityl, methoxymethyl, methoxyethoxymethyl, ethoxyethyl, tetrahydropyranyl, tetrahydrothiopyranyl, and trialkylsilyl ethers such as trimethylsilyl ether, triethylsilyl ether, dimethylarylsilyl ether, triisopropylsilyl ether and t-butyldimethylsilyl ether; esters such as benzoyl, acetyl, phenylacetyl, formyl, mono-, di-, and trihaloacetyl such as chloroacetyl, dichloroacetyl, trichloroacetyl, trifluoroacetyl; and carbonates including but not limited to alkyl carbonates having from one to six carbon atoms such as methyl, ethyl, n-propyl, isopropyl, n-butyl, t-butyl; isobutyl, and n-pentyl; alkyl carbonates having from one to six carbon atoms and substituted with one or more halogen atoms such as 2,2,2-trichloroethoxymethyl and 2,2, 2-trichloro-ethyl; alkenyl carbonates having from two to six carbon atoms such as vinyl and allyl; cycloalkyl carbonates have from three to six carbon atoms such as cyclopropyl, cyclobutyl, cyclopentyl and cyclohexyl; and phenyl or benzyl carbonates optionally substituted on the ring with one or more $C_{1-6}$ alkoxy, or nitro. Other hydroxyl, sulfhydryl and amine protecting groups may be found in "Protective Groups in Organic Synthesis" by T. W. Greene, John Wiley and Sons, 1981.

The alkyl groups described herein, either alone or with the various substituents defined hereinabove are preferably lower alkyl containing from one to six carbon atoms in the principal chain and up to 15 carbon atoms. They may be straight or branched chain and include methyl, ethyl, propyl, isopropyl, butyl, isobutyl, tert-butyl, aryl, hexyl, and the like.

The alkenyl groups described herein, either alone or with the various substituents defined hereinabove are preferably lower alkenyl containing from two to six carbon atoms in the principal chain and up to 15 carbon atoms. They may be straight or branched chain and include ethenyl, propenyl, isopropenyl, butenyl, isobutenyl, aryl, hexenyl, and the like.

The alkynyl groups described herein, either alone or with the various substituents defined hereinabove are preferably lower alkynyl containing from two to six carbon atoms in the principal chain and up to 15 carbon atoms. They may be straight or branched chain and include ethynyl, propynyl, butynyl, isobutynyl, aryl, hexynyl, and the like.

The aryl moieties described herein, either alone or with various substituents, contain from 6 to 15 carbon atoms and include phenyl. Substituents include alkanoxy, protected hydroxy, halogen, alkyl, aryl, alkenyl, acyl, acyloxy, nitro, amino, amido, etc. Phenyl is the more preferred aryl.

The heteroaryl moieties described herein, either alone or with various substituents, contain from 5 to 15 atoms and include, furyl, thienyl, pyridyl and the like. Substituents include alkanoxy, protected hydroxy, halogen, alkyl, aryl, alkenyl, acyl, acyloxy, nitro, amino, amido, etc.

The acyloxy groups described herein contain alkyl, alkenyl, alkynyl, aryl or heteroaryl groups.

In accordance with the present invention, it has been discovered that the C9 keto substituent may be selectively reduced to yield the corresponding C9 β-hydroxy derivative. The reducing agent is preferably a borohydride and, most preferably, tetralbutylammoniumborohydride ($Bu_4NBH_4$) or triacetoxyborohydride.

As illustrated in Reaction Scheme 1, the reaction of baccatin III with $Bu_4NPH_4$ in methylene chloride yields 9-desoxo-9β-hydroxybaccatin III 5. After the C7 hydroxy group is protected with, for example, the triethylsilyl protecting group, a suitable side chain may be attached to 7-protected-9β-hydroxy derivative 6 as set forth in U.S. Pat. Nos. 4,924,011 and 4,924,012 or by reaction with a β-lactam as set forth in U.S. Pat. No. 5,175,315 or copending U.S. patent application Ser. No. 07/349,107. Removal of the remaining protecting groups thus yields 9β-hydroxy-desoxo taxol or other 9β-hydroxytetracylic taxane having a C13 side chain.

Reaction Scheme 1

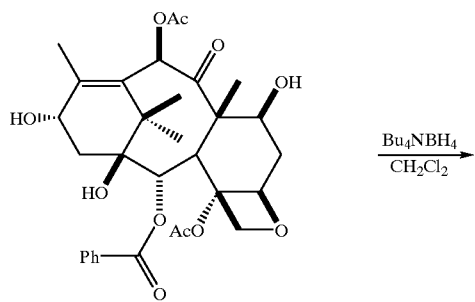

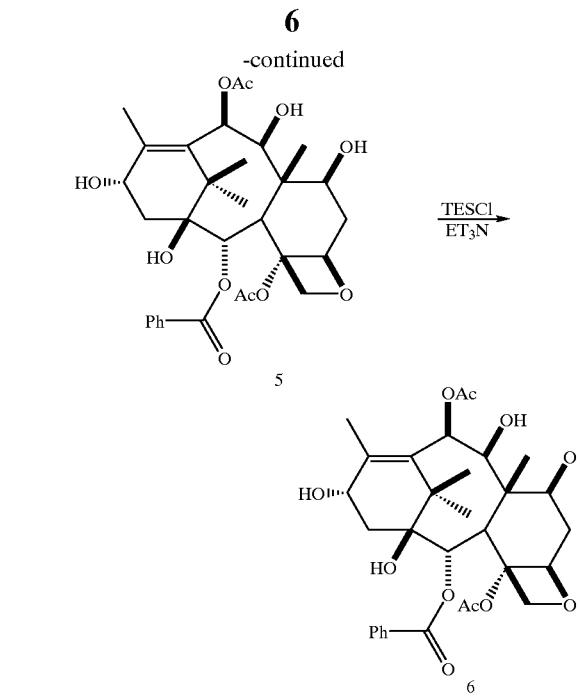

Alternatively, the C13 hydroxy group of 7-protected-9β-hydroxy derivative 6 may be protected with trimethylsilyl or other protecting group which can be selectively removed relative to the C7 hydroxy protecting group as illustrated in Reaction Scheme 2, to enable further selective manipulation of the C8 and C9 functional groups. For example, reaction of 7,13-protected-9β-hydroxy derivative 7 with KH causes the acetate group to migrate from C10 to C9 and hydroxy group to migrate from C9 to C10, thereby yielding lo-desacetyl derivative 8. Protection of the C10 hydroxy group of 10-desacetyl derivative 8 with triethylsilyl yields derivative 9. Selective removal of the C13 hydroxy protecting group from derivative 9 yields derivative 10 to which a suitable side chain may be attached as described above.

Reaction Scheme 2

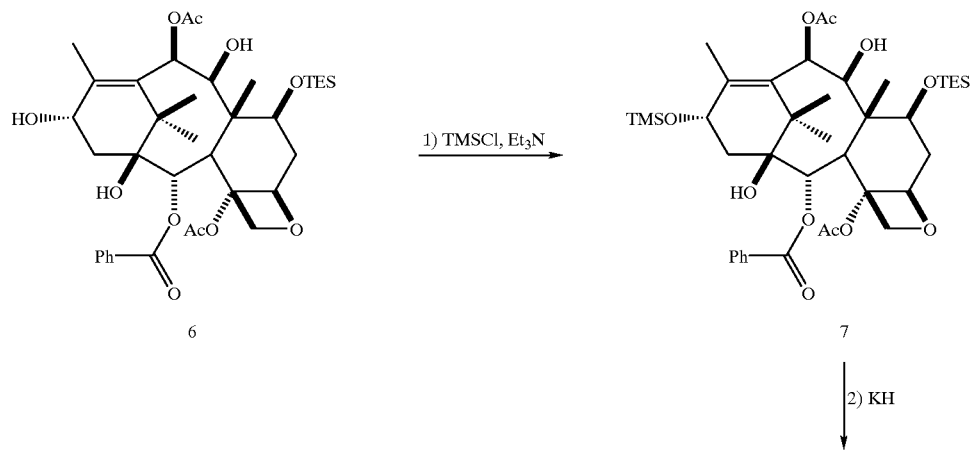

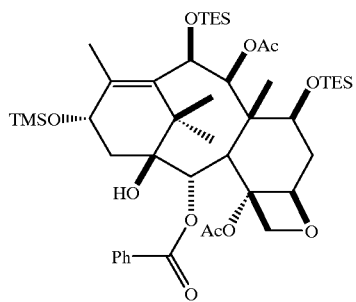

7

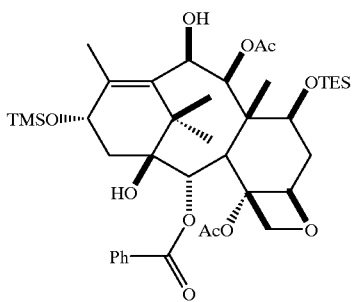

8

TESCl / ET₃N (arrow from 8 to 9)

9

HF / pyridine

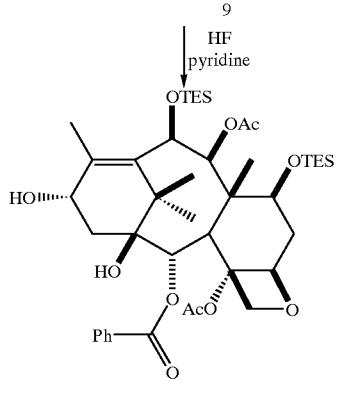

10

As shown in Reaction Scheme 3, 10-oxo derivative 11 can be provided by oxidation of 10-desacetyl derivative 8. Thereafter, the C13 hydroxy protecting group can be selectively removed followed by attachment of a side chain as described above to yield 9-acetoxy-10-oxo-taxol or other 9-acetoxy-10-oxotetracylic taxanes having a C13 side chain. Alternatively, the C9 acetate group can be selectively removed by reduction of 10-oxo derivative 11 with a reducing agent such as samarium diiodide to yield 9-desoxo-10-oxo derivative 12 from which the C13 hydroxy protecting group can be selectively removed followed by attachment of a side chain as described above to yield 9-desoxo-10-oxo-taxol or other 9-desoxo-10-oxotetracylic taxanes having a C13 side chain.

Reaction Scheme 3

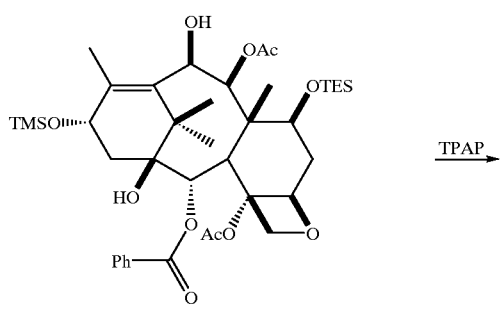

8

TPAP

-continued

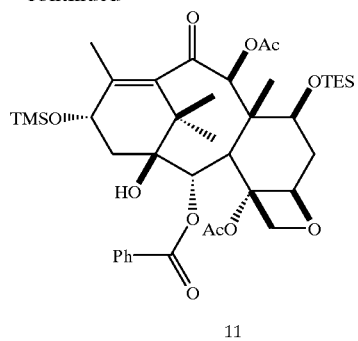

11

SmI₂

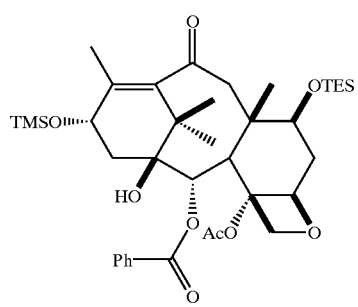

12

Reaction Scheme 4 illustrates a series of reactions in which 10-DAB is used as the starting material. Reduction of 10-DAB yields pentaol 13, the C7 and C10 hydroxyl groups of which can be selectively protected with the triethylsilyl or another protecting group to produce triol 14. A C13 side chain can be attached to triol 14 as described above or, alternatively, after further modification of the tetracyclic substituents.

Reaction Scheme 4

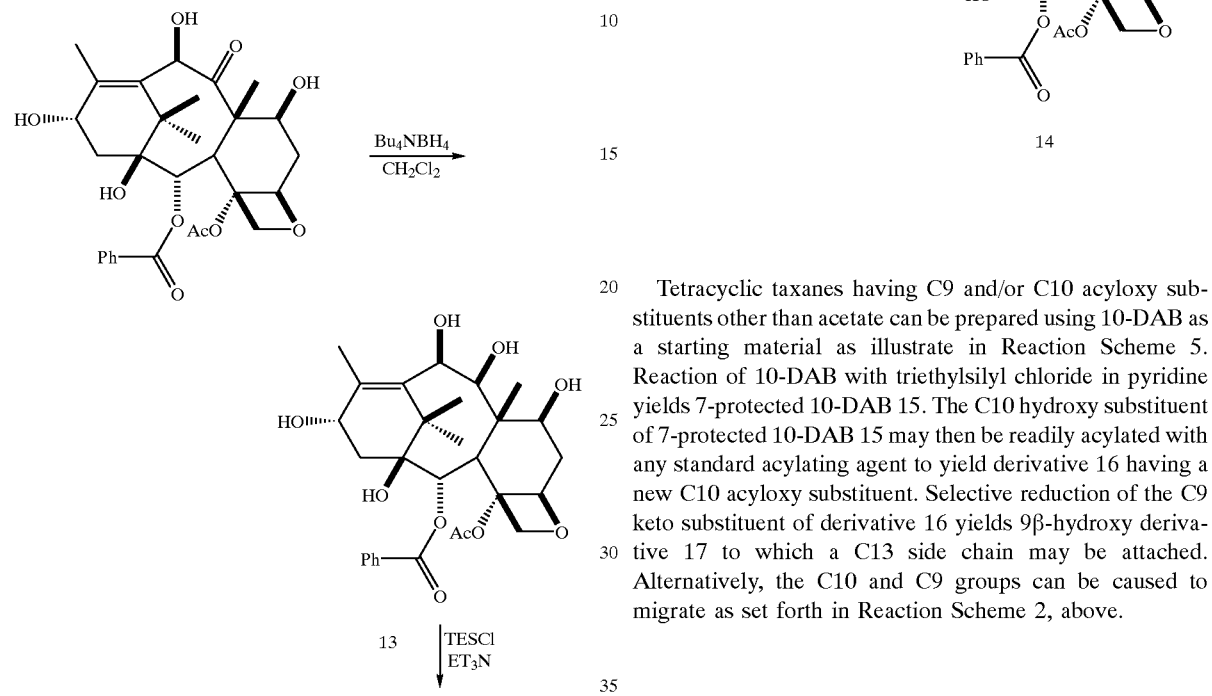

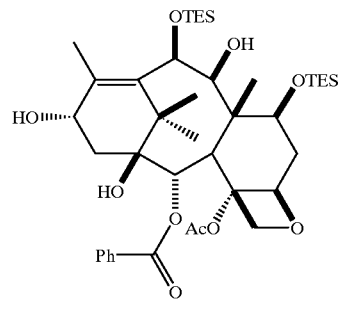

Tetracyclic taxanes having C9 and/or C10 acyloxy substituents other than acetate can be prepared using 10-DAB as a starting material as illustrate in Reaction Scheme 5. Reaction of 10-DAB with triethylsilyl chloride in pyridine yields 7-protected 10-DAB 15. The C10 hydroxy substituent of 7-protected 10-DAB 15 may then be readily acylated with any standard acylating agent to yield derivative 16 having a new C10 acyloxy substituent. Selective reduction of the C9 keto substituent of derivative 16 yields 9β-hydroxy derivative 17 to which a C13 side chain may be attached. Alternatively, the C10 and C9 groups can be caused to migrate as set forth in Reaction Scheme 2, above.

Reaction Scheme 5

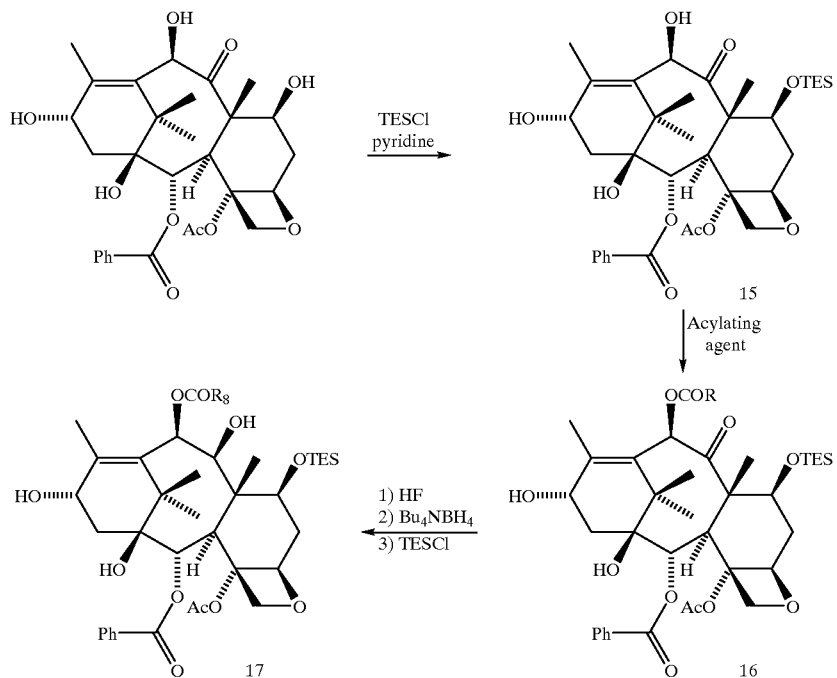

9-deoxo tetracyclic taxanes having alternative C2 and/or C4 esters can be prepared using baccatin III and 10-DAB as starting materials. The C2 and/or C4 esters of baccatin III and 10-DAB can be selectively reduced to the corresponding alcohol(s) using reducing agents such as LAH or Red-Al, and new esters can thereafter be substituted using standard acylating agents such as anhydrides and acid chlorides in combination with an amine such as pyridine, triethylamine, DMAP, or diisopropyl ethyl amine. Alternatively, the C2 and/or C4 alcohols may be converted to new C2 and/or C4 esters through formation of the corresponding alkoxide by treatment of the alcohol with a suitable base such as LDA followed by an acylating agent such as an acid chloride. Baccatin III and 10-DAB analogs having different substituents at C2 and/or C4 can be prepared as set forth in Reaction Schemes 6–10. To simplify the description, 10-DAB is used as the starting material. It should be understood, however, that baccatin III derivatives or analogs may be produced using the same series of reactions (except for the protection of the C10 hydroxy group) by simply replacing 10-DAB with baccatin III as the starting material. 9-desoxo derivatives of the baccatin III and 10-DAB analogs having different substituents at C2 and/or C4 can then be prepared by reducing the C9 keto substituent of these analogs and carrying out the other reactions described above.

In Reaction Scheme 6, protected 10-DAB 3 is converted to the triol 18 with lithium aluminum hydride. Triol 18 is then converted to the corresponding C4 ester using $Cl_2CO$ in pyridine followed by a nucleophilic agent (e.g., Grignard reagents or alkyllithium reagents).

Alternatively, deprotonation of triol 18 with LDA followed by introduction of an acid chloride selectively gives the C4 ester. For example, when acetyl chloride was used, triol 18 was converted to 1,2 diol 4 as set forth in Reaction Scheme 7.

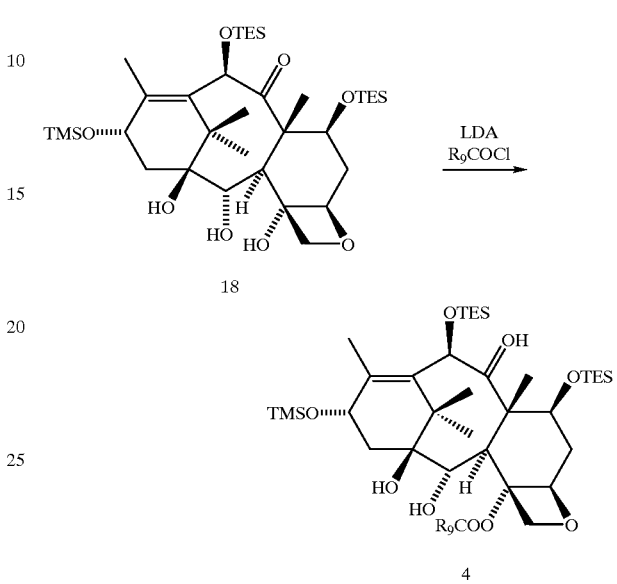

Triol 18 can also readily be converted to the 1,2 carbonate 19. Acetylatio. of carbonate 19 under vigorous standard conditions provides carbonate 21 as described in Reaction

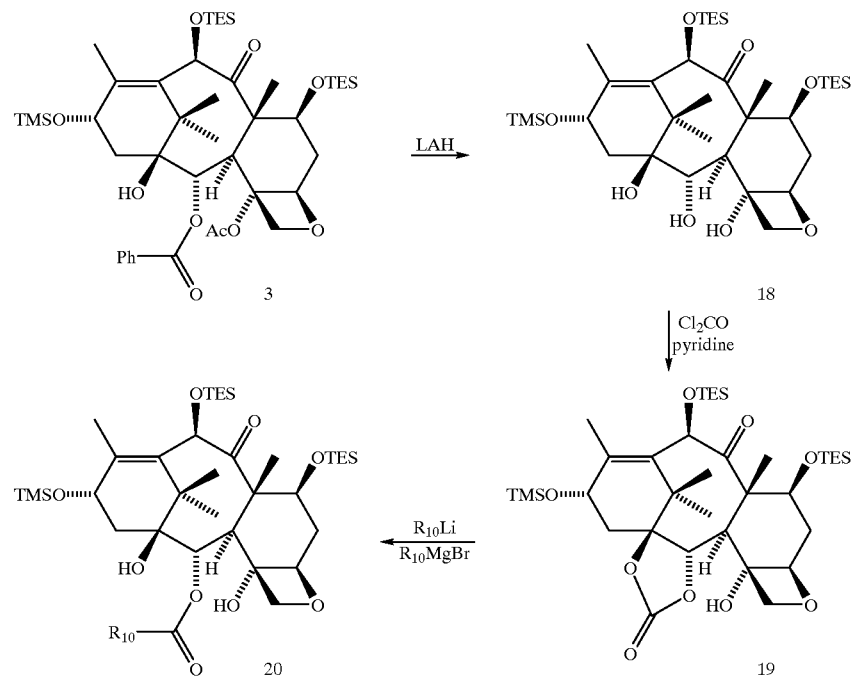

Scheme 8; addition of alkyllithiums or Grignard reagents to carbonate 19 provides the C2 ester having a free hydroxyl group at C4. As set forth in Reaction Scheme 9, other C4 substituents can be provided by reacting carbonate 19 with an acid chloride and a tertiary amine to yield carbonate 22 which is then reacted with alkyllithiums or Grignard reagents to provide 10-DAB derivatives having new substituents at C2 as set forth in Reaction Scheme 8.

Scheme 8

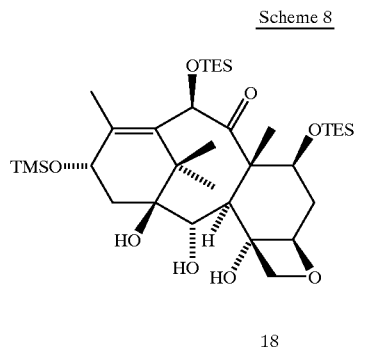

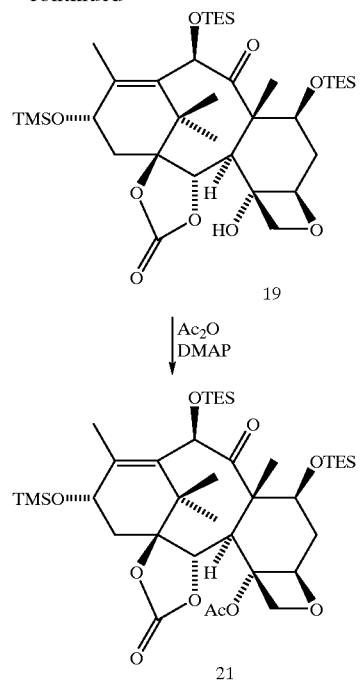

Scheme 9

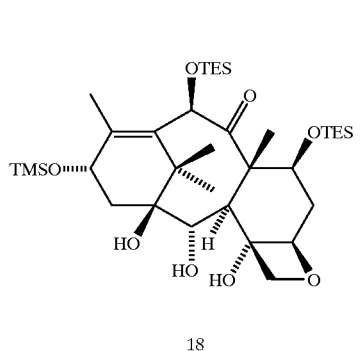

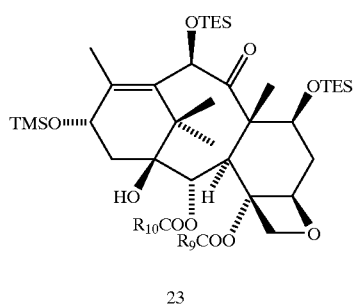

Alternatively, baccatin III may be used as a starting material and reacted as shown in Reaction Scheme 10. After being protected at C7 and C13, baccatin III is reduced with LAH to produce 1,2,4,10 tetraol 24. Tetraol 24 is converted to carbonate 25 using $Cl_2CO$ and pyridine, and carbonate 25 is acylated at C10 with an acid chloride and pyridine to produce carbonate 26 (as shown) or with acetic anhydride and pyridine (not shown). Acetylation of carbonate 26 under vigorous standard conditions provides carbonate 27 which is then reacted with alkyl lithiums to provide the baccatin III derivatives having new substituents at C2 and C10.

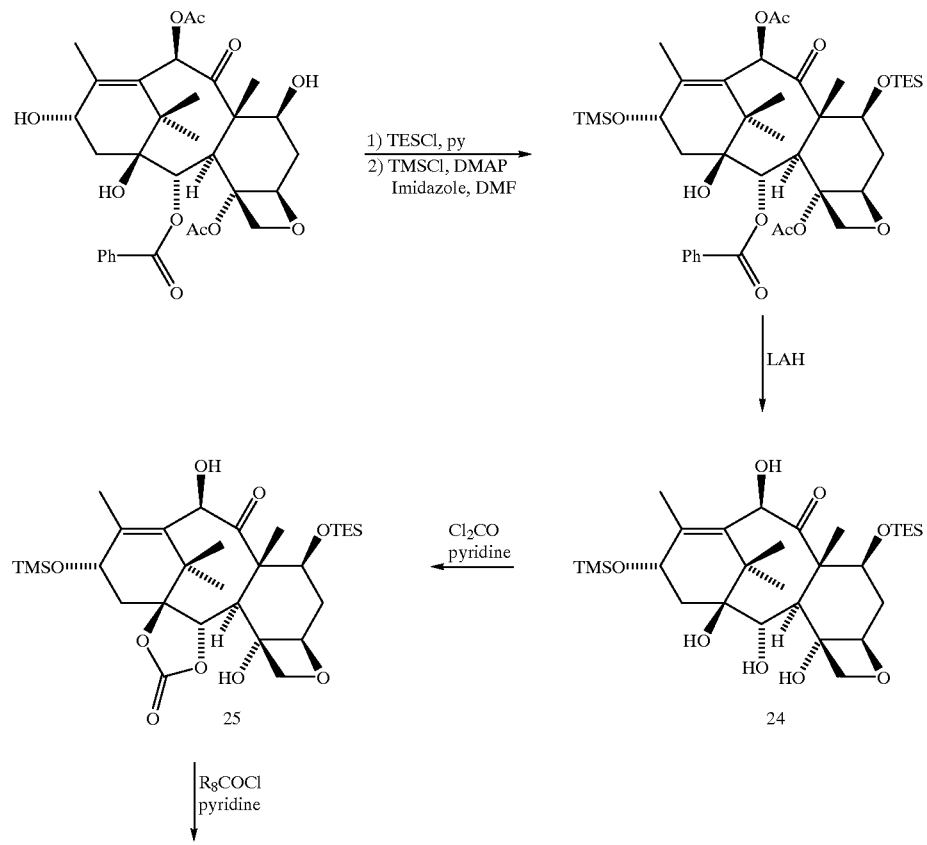

Scheme 10

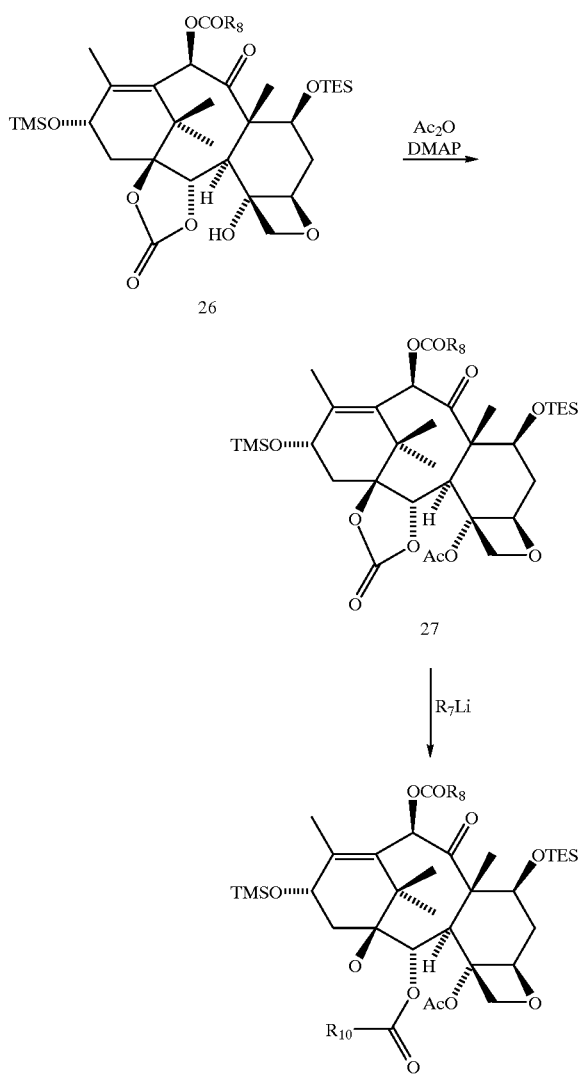

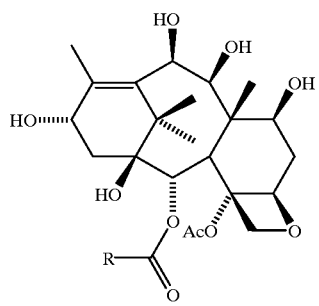

EXAMPLE 1

10-Deacetyl-9β-hydroxy-9-deoxo baccatin (III). A mixture of 10-deacetyl baccatin (III) (300 mg, 0.55 mmol) and n-Bu$_4$NBH$_4$ (709 mg, 2.76 mmol) in 50 mL of CH$_2$Cl$_2$ was stirred for 12 h at room temperature. The resulting mixture was diluted with ethyl acetate, and quenched by stirring with aqueous NaHCO$_3$ solution for 20 min. The organic layer was washed with aqueous NaHCO$_3$ and brine, dried over Na$_2$SO$_4$ and concentrated to give a residue which was purified by flash chromatography. Elution with ethyl acetate—methanol(50:1) afforded 256 mg (85%) of 10-deacetyl-9β-hydroxy-9-deoxo baccatin (III) which was recrystallized from CH$_2$Cl$_2$. m.p. 209–210° C.; [α]$^{25}$Na+ 14.67° (c 0.15, MeOH) $^1$H NMR (CD$_3$OD, 500 MHz) δ 8.11 (m, 2H, benzoate ortho), 7.61 (m, 1H, benzoate, para), 7.49 (m, 2H, benzoate, meta), 6.11 (d, J=5.5 Hz, 1H, H2), 5.09 (d, J=5.5 Hz, 1H, H10), 4.99 (d, J=8.5 Hz, 1H, H5), 4.80 (ddd, J=10.0, 6.0, 1.5 Hz, 1H, H13), 4.55 (d, J=5.5 Hz, 1H, H9α), 4.23 (d, J=8.0 Hz, 1H, H20α), 4.13 (dd, J=8.0, 1.0 Hz, 1H, H20β), 3.89 (dd, J=10.0, 7.0 Hz, 1H, H7), 3.23 (d, J=5.5 Hz, 1H, H3), 2.47 (ddd, J=15.0, 8.5, 7.0 Hz, 1H, H6α), 2.33 (dd, J=15.0, 6.0 Hz, 1H, H14α), 2.21 (s, 3H, 4Ac), 2.20 (ddd, J=15.0, 10.0, 1.0 Hz, 1H, H14β), 1.91 (d, J=1.5 Hz, 3H, Me18), 1.83 (ddd, J=15.0, 10.0, 1.0 Hz, 1H, H6β), 1.72 (s, 3H, Me16), 1.59 (s, 3H, Me19), 1.16 (s, 3H, Me17).

EXANPLE 2

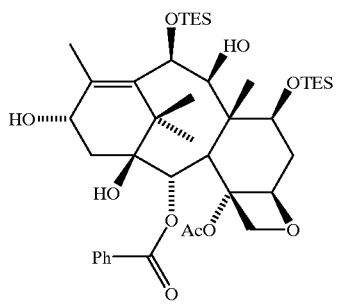

7,10-bis-O-Triethylsilyl-10-deacetyl-9β-hydroxy-9-deoxo baccatin (III). To a stirred solution of 10-deacetyl-9β-hydroxy-9-deoxo baccatin (III) (50 mg, 91.6 mmol) and triethylamine (128 mL, 916 mmol) in THF (0.35 mL) was added chlorotriethylsilane (185 mL, 641 mmol), and the reaction mixture was stirred for 24 h at room temperature. The resulting mixture was diluted with ethyl acetate and 9-desoxo-10-desacetoxy derivatives of baccatin III and 9-desoxo-10-desoxy derivatives of 10-DAB may be prepared by reacting baccatin III or 10-DAB (or their derivatives) with samarium diiodide and thereafter reducing the C9 keto substituent as otherwise described herein. Reaction between the tetracyclic taxane having a C10 leaving group and samarium diiodide may be carried out at 0° C. in a solvent such as tetrahydrofuran. Advantageously, the samarium diiodide selectively abstracts the C10 leaving group; C13 side chains and other substituents on the tetracyclic nucleus remain undisturbed.

The following examples are provided to more fully illustrate the invention.

washed with aqueous NaHCO₃ and brine. The organic layer was dried over Na₂SO₄ and evaporated to give a residue, which was purified by flash chromatography. Elution with hexane-ethyl acetate (1:1) afforded 53 mg (75%) of 7,10-bis-O-triethyl-silyl-10-deacetyl-9β-hydroxy-9-deoxo baccatin (III). ¹H NMR (CDCl₃, 500 MHz) δ 8.11 (m, 2H, benzoate ortho), 7.57 (m, 1H, benzoate, para), 7.47 (m, 2H, benzoate, meta), 6.22 (d, J=5.0 Hz, 1H, H2), 5.03 (d, J=5.5 Hz, 1H, H10), 4.88 (d, J=8.7 Hz, 1H, H5), 4.81 (m, 1 H, H13), 4.45 (d, J=5.5 Hz, 1H, H9α), 4.35 (d, J=8.2 Hz, 1H, H20α), 4.22 (d, J=8.2 Hz, 1H, H20β), 3.97 (dd, J=9.2, 7.8 Hz, 1H, H7), 3.15 (d, J=5.0 Hz, 1H, H3), 2.54 (m, 1H, H6α), 2.31 (dd, J=15.5, 10.5 Hz, 1H, H14), 2.29 (s, 3H, 4Ac), 2.01 (dd, J=15.5, 6.4 Hz, 1H, H14), 1.95 (d, J=1.5 Hz, 3H, Me18), 1.94 (m, 1H, H6β), 1.74 (s, 3H, Me16), 1.63 (s, 3H, Me19), 1.16 (s, 3H, Me17) 0.99 (m, 9H, triethylsilyl), 0.67 (m, 6H, triethylsilyl).

EXAMPLE 3

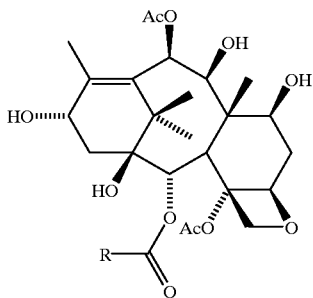

9β-Hydroxy-9-deoxo baccatin III. To a solution of baccatin III (215 mg, 0.367 mmol) in 5 mL of CH₂Cl₂ was added n-Bu₄NBH₄ (944 mg, 3.67 mmol) and the mixture was stirred for 48 h at room temperature. The resulting mixture was diluted with ethyl acetate, and quenched by stirring with aqueous NaHCO₃ solution for 20 min. The organic layer was washed with aqueous NaHCO₃ and brine, dried over Na₂SO₄ and concentrated to give a residue which was separated by flash chromatography. Elution with CH₂Cl₂-acetone (2:1) afforded 111 mg (51%) of 9β-hydroxy-9-deoxo baccatin (III), which was recrystallized from ethyl acetate-ether-hexane. m.p.160–162° C.; [α]²⁵Na −3.6° (c 0.055, CHCl₃) ¹H NMR (CDCl₃, 500 MHz) δ 83.11 (m, 1H, benzoate ortho), 7.59 (m, 1H, benzoate, para), 7.47 (m, 2H, benzoate, meta), 6.20 (d, J=5.0 Hz, 1H, H2β), 6.16 (d, J=5.5 Hz, 1H, H10), 4.95 (d, J=6.5 Hz, 1H, H5), 4.82 (dd, J=8.5, 7.0 Hz, 1 H, H13), 4.44 (d, J=5.0 Hz, 1H, H9), 4.37 (d, J=8.0 Hz, 1H, H20α), 4.21 (d, J=8.0 Hz, 1H, H:20β), 4.08 (br t, J=8.0 Hz, 1H, H7), 3.18 (d, J=5.0 Hz, 1H, H3), 2.55 (ddd, J=15.0, 8.0, 7.0 Hz, 1H, H6α), 2.32 (ddd, J=15.5, 10.0, 1.0 Hz, 1H, H14β), 2.30 (s, 3H, 4Ac), 2.16 (s, 3H, 10Ac), 2.09 (d, J=1.5 Hz, 3H, Me18), 2.04 (dd, J=15.5, 6.5 Hz, 1H, H14α), 1.90 (ddd, J=15.0, 9.0, 2.0 Hz, 1H, H6β), 1.69 (s, 3H, Me16) 1.66 (s, 3H, Me19), 1.11 (,s, 3H, Me17).

EXAMPLE 4

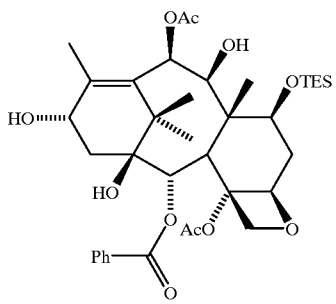

7-O-Triethylsilyl-9β-hydroxy-9-deoxo baccatin (III). To a To a solution of triethylamine (0.330 mL, 2.35 mmol) in THF (36 mL) at 0° C. was added triethylsilyl chloride (0.39 mL, 2.35 mmol). To this mixture was added a solution of 9β-hydroxy-9-deoxo baccatin (III) (276 mg, 0.47 mmol) in 10 mL of THF. The solution was warmed to room temperature and stirred for 49 h. MeOH (1 mL) was added and the mixture was stirred for 10 min. The resulting solution was poured into saturated aqueous NaHCO₃ (100 mL) and extracted with ethyl acetate (2×150 mL). The organic layer was washed with saturated aqueous NaHCO₃ (100 mL) and brine (100 mL), dried over Na₂SO₄, filtered, and concentrated under reduced pressure to give a crude residue (0.3 g). Flash column chromatography (CH₂Cl₂-ethyl acetate) afforded 7-O-triethylsilyl-9β-hydroxy-9-deoxo baccatin (III) (297 mg, 89%). ¹H-NMR (CDCL₃, 500 Mz), δ 8.11 (dd, J=1, 7.5 Hz, 2H benzoate ortho), 7.56–7.59 (m, 1H, benzoate), 7.45–7.48 (m, 2H, benzoate), 6.20 (d, J=5 Hz, 1H, H-2), 6.16 (d, J=5.5 Hz, 1H, H10), 4.88 (d, J=9 Hz, 1H, H-5),4.84 (m, 1H, H-13), 4.63 (br-d, J=6 Hz, 1H, H-9), 4.36 (d, J=9 Hz, 1H, H-20α), 4.20 (d, J=9 Hz, 1H, H-20β), 3.93 (dd, J=7, 8.5 Hz, 1H, H-7) 3.19 (d, J=5 Hz, 1H, H-3), 2.63 (br-d, J=4 Hz, 1H, OH-9), 2.51 (m, 1H, H-6α), 2.47 (d, J=6 Hz, 1H, OH-10), 2.32 (dd, J=10, 16 Hz, 1H, H-14β), 2.29 (s, 3H, Ac), 2.21 (d, J=9 Hz, 1H, OH-13), 2.17 (s, 1H, OH-1), 2.03 (m, 1H, H-14α), 1.98 (d, J=1.5 Hz, 3H, Me-18), 1.93 (ddd, J=1.5, 9.5 15 Hz, 1H, H-6β), 1.74 (s, 3H, Me-16), 1.63 (s, 3H, Me-19), 1.17 (s, 3H, Me-17), 0.99 (t, J=7.5 Hz, 9H, SiCH2CH3), 0.63 and 0.64 (q×2, J=7.5 Hz, 6H, SiCH2CH3).

EXAMPLE 5

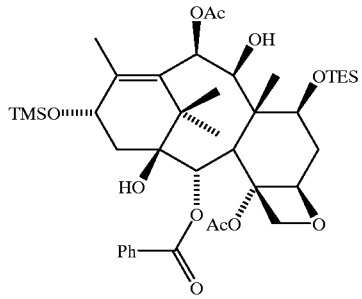

7-O-Triethylsilyl-9β-hydroxy-9-deoxo-13-O-trimethylsilyl baccatin (III). To a stirred solution of 7-O-triethylsilyl-9β-hydroxy-9-deoxo baccatin (III) (140 mg; 0.196 mmol) in anhydrous pyridine (0.7 mL,) at room temperature TMSCl (0.24 mL; 1.9 mmol) was added. After stirring for 36 h the reaction mixture was diluted with ethyl acetate (50 mL) and the mixture was poured into saturated aqueous NaHCO₃ (25 mL). The organic phase was washed with saturated aqueous NaHCO₃ and brine, dried over Na₂SO₄ and evaporated. The product was isolated by filtration through a small pad of SiO₂ eluting with 15% EA-hexanes affording 140 mg (94%) of 7-O-triethylsilyl-9β-hydroxy-9-deoxo-13-O-trimesthylsilyl baccatin (III). ¹H-nmr (300 MHz, CDCL₃) δ 8.10 (dd ; 2H; J=7.7, 1.1 Hz; o-Bz); 7.58 (t; 1H; J=7.7 Hz; p-Bz); 7.46 (br t; 2H; J=7.7 Hz; m-Bz); 6.12 (d; 1H; J=5.0 Hz; H-2β); 6.10 (d; 1H; J=3.8 Hz; H-10α); 5.00 (br t; 1H; J=8.2 Hz; H-13β); 4.93 (d; 1H; J=8.8 Hz; H-5α); 4.58 (br d; 1H; J=3.8 Hz; H-9α; 4.33 (d; 1H; J=8.2 Hz; H-20α); 4.14 (d; 1H; J=8.2 Hz; H-20β); 4.01 (dd; 1H; J=8.8, 7.7 Hz; H-7α); 3.12 (d; 1H; J=5.0 Hz; H-3α); 2.53 (ddd; 1H; J=14.8, 8.8, 7.7 Hz; H-6a), 2.23 (s; 3H; 4-OAc); 2.21 (br s; 1H; 9-OH); 2.20 (dd; 1H; J=14.0, 8.2 Hz; H-14a); 2.11 (s; 3H; 10-OAc); 2.07 (dd; 1H; J=14.0, 8.2 Hz; H-14β); 2.04 (br s; 3H; 18-Me); 1.89 (brdd; 1H; J=14.8, 9.9 Hz; H-6β); 1.76 (s; 1H; 1-OH); 1.74 (s; 3H; 16-Me); 1.59 (s, 3H; 19-Me); 1.19 (s, 3H; 17-Me); 0.95 (t; 9H; J=8.0 Hz; 7-TES-Me); 0.65 (m; 6H; TES-CH₂); 0.01 (s, 9H; TMS).

EXAMPLE 6

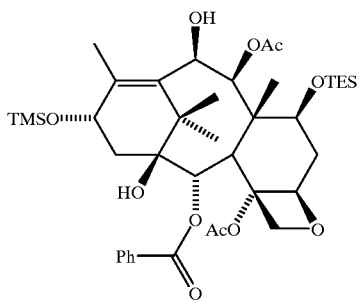

7-O-Triethylsilyl-9β-acetoxy-9-deoxo-10-deacetyl-13-O-trimethylsilyl baccatin (III). To a stirred suspension of KH (250 mg, 35% in mineral oil, washed 3×1 mL with pentane; 2.19 mmol) in anhydrous THF (2.5 mL) a solution of 7-O-triethyl-silyl-9β-hydroxy-9-deoxo-13-O-trimethylsilyl baccatin (III) (142 mg; 0.18 mmol) in anhydrous THF (4 mL) was added at 0° C. After 5 min the mixture was warmed up to room temperature and stirred for 30 min and then cooled down to −10° C. The reaction mixture was quenched with AcOH in THF solution (1.6M; 0.15 mL) and stirred for 5 min at the same temperature before diluting with ethyl acetate (50 ml). The mixture was poured into saturated aqueous NaHCO₃ (50 mL) and the organic phase was washed with brine, dried over Na₂SO₄ and evaporated. The product was isolated by flash chromatography (SiO₂; 25% ethyl acetate-hexanes) affording 29 mg of recovered starting material (21%) and 107 mg (75%) of 7-O-triethylsilyl-9β-acetoxy-9-deoxo-10-deacetyl-13-O-trimethylsilyl baccatin (III). ¹H-nmr (500 MHz, CDCl₃) δ 8.10 (br dd ; 2H; J=7.3, 1.1 Hz; o-Bz); 7.59 (tt; 1H; J=7.3, 1.3 Hz; p-Bz); 7.43 (br t; 2H; J=7.3 Hz; m-Bz); 6.09 (d; 1H; J=5.9 Hz; H-9α); 6.04 (br d; 1H; J=4.8 Hz; H-2β); 5.25 (dd; 1H; J=5.9, 1.5 Hz; H-10α); 5.05 (br t; 1H; J=8.6 Hz; H-13β); 4.92 (br d; 1H; J=8.8 Hz; H-5α); 4.32 (br d; 1H; J=8.4 Hz; H-20α); 4.09 (dd; 1H; J=8.4, 0.7 Hz; H-20β); 4.02 (dd; 1H; J=9.2, 7.7 Hz; H-7α); 3.23 (br d; 1H; J=4.8 Hz; H-3α); 2.56 (ddd; 1H; J=15.0, 9.5, 7.7 Hz; H-6α); 2.26 (s; 3H; 9-OAc); 2.24 (S; 3H; 4-OAc); 2.21 (dd; 1H; J=15.0, 7.7 Hz; H-14α); 2.16 (d; 1H; J=1.5 Hz; 10-OH); 2.12 (br dd; 1H; J=15.0, 9.7 Hz; H-14β); 1.93 (d; 3H; J=1.1 Hz; 18-Me); 1.89 (brdd; 1H; J=:15.0, 9.2, 1.1 Hz; H-6β); 1.715 (s; 3H; 16-Me); 1.71 (s; 1H; 1-OH); 1.42 (s, 3H; 19-Me); 1.28 (s, 3H; 17-Me); 1.02 (t; 9H; J=8.0 Hz; TES-Me); 0.68 (m; 6H; TES-CH₂); 0.01 (s, 9H; TMS)

EXAMPLE 7

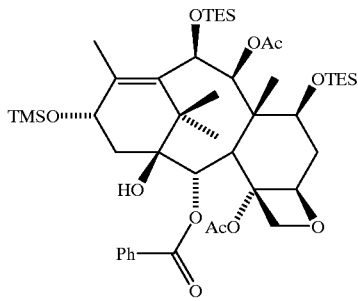

7,10-bis-O-Triethylsilyl-9β-acetoxy-9-deoxo-10-deacetyl-13-O-trimethylsilyl baccatin (III). To a solution of 7-O-triethylsilyl-9β-hydroxy-9-deoxo-13-O-trimethylsilyl baccatin (III) (72 mg; 0.09 mmol) and triethylamine (128 mL, 916 mmol) in THF (0.35 mL) was added chlorotriethylsilane (185 mL, 641 mmol), and the reaction mixture was stirred for 24 h at room temperature. The resulting mixture was diluted with ethyl acetate and washed with aqueous NaHCO₃ and brine. The organic layer was dried over Na₂SO₄ and concentrated to give a residue, which was purified by flash chromatography. Elution with hexane-ethyl acetate (1:1) afforded 63 mg (75%) of 7,10-bis-O-triethylsilyl-9β-acetoxy-9-deoxo-10-deacetyl-13-O-trimethylsilyl baccatin (III). ¹H-nmr (500 MHz, CDCL₃) δ 8.10 (br dd ; 2H; J=7.3, 1.1 Hz; o-Bz); 7.59 (tt; 1H; J=7.3, 1.3 Hz; p-Bz); 7.43 (br t; 2H; J=7.3 Hz; m-Bz); 6.09 (d; 1H; J=5.9 Hz; H-9α); 6.04 (br d; 1H; J=4.8 Hz; H-2β); 5.10 (d; 1H; J=5.5; H-10α); 5.05 (br t; 1H; J=8.6 Hz; H-13β); 4.92 (br d; 1H; J=8.8 Hz; H-o5α); 4.32 (br d; 1H; J=8.4 Hz; H-20α); 4.09 (dd; 1H; J=8.4, 0.7 Hz; H-20β); 4.02 (dd; 1H; J=9.2, 7.7 Hz; H-7α); 3.23 (br d; 1H; J=4.8 Hz; H-3α); 2.56 (ddd; 1H; J=15.0, 9.5, 7.7 Hz; H-6α); 2.26 (s; 3H; 9-OAc); 2.24 (s; 3H; 4-OAc); 2.21 (dd; 1H; J=15.0, 7.7 Hz; H-14α); 2.12 (br dd; 1H; J=15.0, 9.7 Hz; H-14β); 1.93 (d; 3H; J=1.1 Hz; 18-Me); 1.89 (brdd; 1H; J=15.0, 9.2, 1.1 Hz; H-6β); 1.715 (s; 3H; 16-Me,); 1.71 (s; 1H; 1-OH); 1.42 (s, 3H; 19-Me); 1.28 (s, 3H; 17-Me); 1.02 (t; 9H; J=8.0 Hz; TES-Me); 0.68 (m; 6H; TES-CH₂); 0.01 (s, 9H; TMS)

EXAMPLE 8

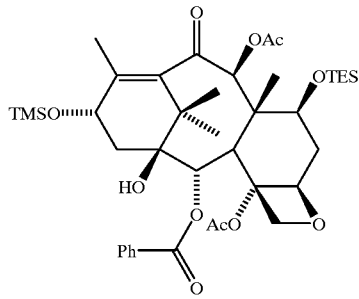

7-O-Triethylsilyl-9β-acetoxy-9-deoxo-10-deacetoxy-10-oxo-13-O-trimethylsilyl baccatin (III). A suspension of 7-O- triethylsilyl-9β-acetoxy-9-deoxo-10-deacetyl-13-O-trimethylsilyl baccatin (III) (47 mg; 0.06 mmol), NMO (9 mg; 0.077 mmol) and powdered 4A molecular sieves (25 mg) in anhydrous CH$_2$Cl$_2$ (2.5 mL) was stirred at room temperature for 5 minutes and then a catalytic amount of TPAP was added (1 mg approx.). The mixture was stirred for 1h and then filtered through a small pad of coarse SiO$_2$ eluting with 20% ethyl acetate-hexanes. The filtrate was evaporated affording 45.5 mg (97%) of 7-O-Triethylsilyl-9β-acetoxy-9-deoxo-10-deacetoxy-10-oxo-13-O-trimethylsilyl baccatin (III). $^1$H-nmr (500 MHz, CDCL$_3$) δ 8.16 (br dd ; 2H; J=8.2, 1.2 Hz; o-Bz); 7.61 (br tt; 1H; J=7.3, 1.2 Hz; p-Bz); 7.49 (br t; 2H; J=8.0 Hz; m-Bz); 5.84 (d; 1H; J=5.1 Hz; H-2β); 5.26 (2; 1H; H-9α); 5.00 (br s; 1H; w1/2=8 Hz; H-5α); 4.98 (br t; 1H; J=8.2 Hz; H-13β); 4.43 (dd; 1H; J=7.6, 1.0 Hz; H-20β); 4.23 (dd; 1H; J=7.6, 1.0 Hz; H-20α); 4.23 (br overlapped; 1H; H-7α); 3.57 (br d; 1H; J=5.1 Hz; H-3α); 2.32 (dd; 1H; J=14.9, 7.6 Hz; H-14α); 2.31 (s; 3H; 4-OAc); 2.24 (s; 3H; 9-OAc); 2.17 (br dd; 1H; J=14.9, 8.9 Hz; H-14β); 2.07 (d; 3H; J=1.3 Hz; 18-Me); 2.04 (ddd; 1H; J=1z.9, 3.6, 2.3 Hz; H-6b); 1.97 (ddd; 1H; J=14.9, 3.3, 2.4 Hz; H-6α); 1.79 (s; 1H; 1-OH); 1.44 (s; 3H; 19-Me); 1.32 (s, 3H; 16-Me); 1.25 (s, 3H; 17-Me); 0.93 (t; 9H; J=8.0 Hz; 7-TES-Me); 0.59 (c; 6H; 7-TES-CH$_2$); 0.01 (s, 9H; TMS).

EXAMPLE 9

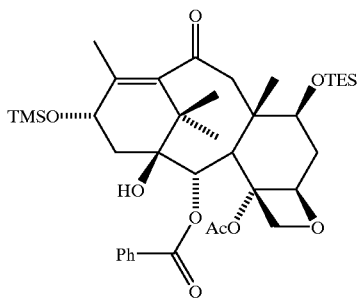

7-O-Triethylsilyl-9-deoxo-10-deacetoxy-10-oxo-13-O-trimethylsilyl baccatin (III). To a stirred solution of 7-O-triethylsilyl-9β-acetoxy-9-deoxo-10-deacetoxy-10-oxo-13-O-trimethylsilyl baccatin (III) (14 mg; 0.018 mmol) in anhydrous THF (0.2 mL) a solution of SmI$_2$ in THF (0.1M; 1 mL) was added under nitrogen at room temperature and the resulting solution was stirred for 1.5 h. The reaction mixture was opened to the air to quench the excess Sm(II), diluted with ethyl acetate (20 mL) and the mixture was poured into ice cold 0.2N HCl and extracted with ethyl acetate; the organic phase was washed with 5% aqueous citric acid, saturated aqueous NaHCO$_3$ and brine, dried over Na$_2$SO$_4$ and evaporated. The product was isolated by flash chromatography (SiO$_2$; 15% ethyl acetate-hexanes) affording 10 mg (81%) of 7-O-triethylsilyl-9-deoxo-10-deacetoxy-10-oxo-3-O-trimethylsilyl baccatin (III). $^1$H-nmr (300 MHz, CDCL$_3$) δ 8.13 (br d ; 2H; J=7.5 Hz; o-Bz); 7.62 (br t; 1H; J=7.5 Hz; p-Bz); 7.49 (br t; 2H; J=7.5 Hz; m-Bz); 5.89 (d; 1H; J=6.0 Hz; H-2β); 4.97 (br t; 1H; J=7.8 Hz; H-13β); 4.91 (d; 1H; J=8.0 Hz; H-5α); 4.33 (br d; 1H; J=8.0 Hz; H-20α); 4.14 (d; 1H; J=8.0 Hz; H-20β); 3.79 (dd; 1H; J=9.0, 6.6 Hz; H-7α); 3.34 (d; 1H; 16.5 Hz; H-9); 3.15 (d; 1H; J=6.0 Hz; H-3α); 2.57 (d; 1H; 16.5 Hz; H-9); 2.49 (ddd; 1H; J=16.5, 9.0, 8.0 Hz; H-6α); 2.25 (s; 3H; 4-OAc); 2.18 (m; 2H; H-14); 1.82 (br s; 3H; 18-Me); 1.75 (ddd; 1H; J=16.5, 6.6, 1.8 Hz; H-6β); 1.72 (s; 1H; 1-OH); 1.48 (s; 3H; Me); 1.38 (s, 3H; Me); 1.23 (s, 3H; Me); 0.99 (t; 9H; J=8.0 Hz; TES-Me); 0.65 (m; 6H; TES-CH$_2$); 0.01 (s, 9H; TMS)

EXAMPLE 10

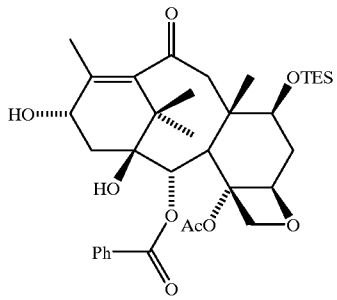

7-O-Triethylsilyl-9-deoxo-10-deacetoxy-10-oxo baccatin (III). To a solution of 7-O-trieihylsilyl-9-deoxo-10-deacetoxy-10-oxo-13-O-trimethylsilyl baccatin (III). (30 mg, 0.025 mmol) in 2.25 mL of acetonitrile and 2.25 mL of THF in a polyethylene vial was added dropwise 0.048 mL of pyridine and 0.075 mL of 48% aqueous HF. The reaction mixture was stirred at room temperature for 12 h and then diluted with ethyl acetate (20 mL). Saturated aqueous sodium bicarbonate was added and the organic layer was separated, washed with brine, dried over anhydrous sodium sulfate and concentrated to give a crude residue. Flash chromatography with 25% ethyl acetate in hexane gave 22 mg (80%) of 7-O-triethylsilyl-9-deoxo-10-deacetoxy-10-oxo baccatin (III). $^1$H-nmr (300 MHz, CDCl$_3$) δ 8.13 (br d; 2H; J=7.5 Hz; o-Bz) 7.62 (br t; 1H; J=7.5 Hz; p-Bz); 7.49 (br t; 2H; J=7.5 Hz; m-Bz); 5.89 (d; 1H; J=6.0 Hz; H-2β); 4.97 (br t; 1H; J=7.8 Hz; H-13β); 4.91 (d; 1H; J=8.0 Hz; H-5α; 4.33 (br d; 1H;J=8.0 Hz; H-20α); 4.14 (d; 1H; J=8.0 Hz; H-20β); 3.79 (dd; 1H; J=9.0, 6.6 Hz; H-7α); 3.34 (d; 1H; 16.5 Hz; H-9); 3.15 (d; 1H; J=6.0 Hz; H-3α); 2.57 (d; 1H; 16.5 Hz; H-9); 2.49 (ddd; 1H; J=16.5, 9.0, 8.0 Hz; H-6α), 2.25 (s; 3H; 4-OAc); 2.18 (m; 2H; H-14); 1.82 (br s; 3H; 18-Me); 1.75 (ddd; 1H; J=16.5, 6.6, 1.8 Hz; H-6β); 1.72 (s; 1H; 1-OH); 1.48 (s; 3H; Me); 1.38 (s, 3H; Me); 1.23 (s, 3H; Me); 0.99 (t; 9H; J=8.0 Hz; TES-Me); 0.65 (m; 6H; TES-CH$_2$).

What we claim is:

1. A tetracylic taxane having the formula

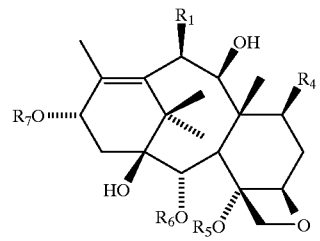

wherein

R$_1$ is H, —OH, protected hydroxy, or —OCOR$_8$,

R$_4$ is —OH or protected hydroxy,

R$_5$ is H or R$_9$CO—,

R$_6$ is H or R$_{10}$OCO—,

R$_7$ is H or a hydroxy protecting group, and

R$_8$, R$_9$, and R$_{10}$ are independently H, C$_1$–C$_6$ alkyl, C$_2$–C$_6$ alkenyl, C$_2$–C$_6$ alkynyl, moncyclic aryl, or monocyclic heteroaryl.

2. The taxane of claim 1 wherein R$_5$ is R$_9$CO— and R$_9$ is methyl.

3. The taxane of claim 2 wherein $R_7$ is hydrogen.

4. The taxane of claim 3 wherein $R_1$ is —$OCOR_8$.

5. The taxane of claim 2 wherein $R_7$ is hydroxy protecting group.

6. The taxane of claim 5 wherein $R_1$ is —$OCOR_8$.

7. The taxane of claim 5 wherein $R_4$ is protected hydroxy.

8. The taxane of claim 1 wherein $R_6$ is $R_{10}OCO$— and $R_{10}$ is phenyl.

9. The taxane of claim 8 wherein $R_7$ is hydrogen.

10. The taxane of claim 9 wherein $R_1$ is —$OCOR_8$.

11. The taxane of claim 8 wherein $R_7$ is hydroxy protecting group.

12. The taxane of claim 11 wherein $R_1$ is —$OCOR_8$.

13. The taxane of claim 1 wherein $R_5$ is $R_9CO$—, $R_6$ is $R_{10}CO$—, $R_9$ is methyl and $R_{10}$ is phenyl.

14. The taxane of claim 13 wherein $R_7$ is hydrogen.

15. The taxane of claim 13 wherein $R_7$ is hydroxy protecting group.

16. The taxane of claim 15 wherein $R_1$ is —$OCOR_8$.

17. The taxane of claim 1 wherein $R_7$ is hydrogen.

18. The taxane of claim 1 wherein $R_7$ is hydroxy protecting group.

19. The taxane of claim 1 wherein $R_1$ is —$OCOR_8$.

\* \* \* \* \*

UNITED STATES PATENT AND TRADEMARK OFFICE
CERTIFICATE OF CORRECTION

PATENT NO.     : 6,291,692 B1
DATED          : September 18, 2001
INVENTOR(S)    : Robert A. Holton, Carmen Somoza, Yukio Suzuki and Mitsuru Shindo It is certified that error appears in the above-identified patent and that said Letters Patent is hereby corrected as shown below:

Column 1,
Line 12, before "BACKGROUND OF THE INVENTION" please insert:
-- This invention was made with Government support under NIH Grant #CA 42031 and NIH Grant #CA 55131 awarded by the National Institutes of Health. The Government has certain rights in the Invention. --

Column 2,
Lines 43-54, Structure 2 should appear as follows:

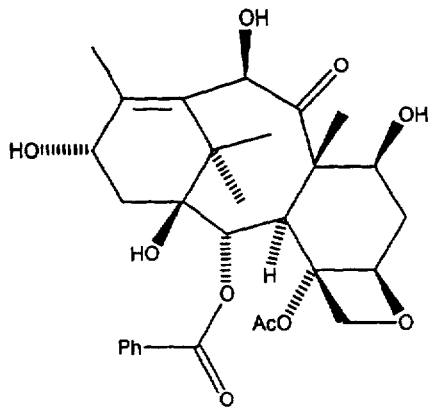

Column 3,
Lines 10-18, the structure should appear as follows:

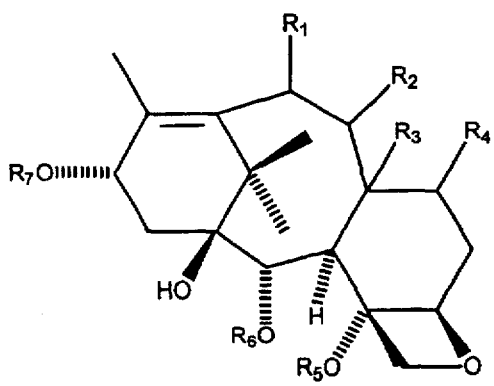

UNITED STATES PATENT AND TRADEMARK OFFICE
CERTIFICATE OF CORRECTION

PATENT NO. : 6,291,692 B1
DATED : September 18, 2001
INVENTOR(S) : Robert A. Holton, Carmen Somoza, Yukio Suzuki and Mitsuru Shindo It is certified that error appears in the above-identified patent and that said Letters Patent is hereby corrected as shown below:

Column 10,
Lines 59-65, Structure 16 should appear as follows:

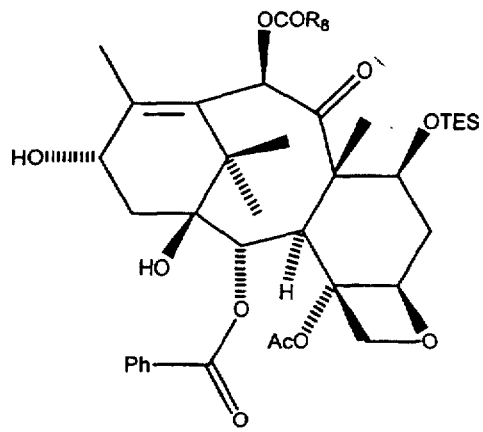

Column 12,
Lines 20-27, Structure 4 should appear as follows:

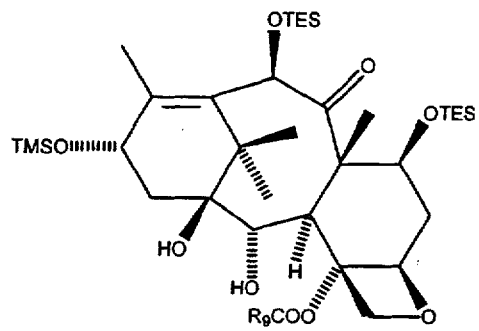

UNITED STATES PATENT AND TRADEMARK OFFICE
CERTIFICATE OF CORRECTION

PATENT NO. : 6,291,692 B1
DATED : September 18, 2001
INVENTOR(S) : Robert A. Holton, Carmen Somoza, Yukio Suzuki and Mitsuru Shindo It is certified that error appears in the above-identified patent and that said Letters Patent is hereby corrected as shown below:

Column 18,
Line 41, "EXANPLE" should read -- EXAMPLE --.

Column 24,
Line 61, "$R_{10}OCO-$" should read -- $R_{10}CO-$ --.

Column 25,
Line 7, "$R_{10}OCO-$" should read -- $R_{10}CO-$ --.

Signed and Sealed this

Seventh Day of May, 2002

*Attest:*

JAMES E. ROGAN
*Attesting Officer*    *Director of the United States Patent and Trademark Office*